United States Patent [19]

Nield et al.

[11] 4,376,868

[45] Mar. 15, 1983

[54] ALKOXYLATION OF CRESYLIC ACIDS

[75] Inventors: Gerald L. Nield; Kang Yang; Paul H. Washecheck, all of Ponca City, Okla.

[73] Assignee: Conoco Inc., Ponca City, Okla.

[21] Appl. No.: 121,351

[22] Filed: Feb. 14, 1980

[51] Int. Cl.³ ..................... C07C 51/00; C07C 41/03
[52] U.S. Cl. ................... 562/465; 568/315; 568/608; 568/609; 568/610; 568/584; 568/586; 568/426; 564/170; 564/413; 564/443; 560/71; 546/134
[58] Field of Search .............. 568/608, 620, 315, 609, 568/610, 584, 586, 426; 564/170, 413, 443; 560/71; 546/134; 562/465

[56] References Cited

U.S. PATENT DOCUMENTS

| 3,009,887 | 11/1961 | Fraiser | 260/2 |
| 3,100,230 | 8/1963 | Mansfield | 568/608 |
| 3,297,783 | 1/1967 | Bailey | 260/836 |
| 3,417,064 | 12/1968 | Bailey | 260/79.5 |
| 3,830,850 | 8/1974 | Stratton | 260/613 B |
| 4,210,764 | 7/1980 | Yang et al. | 568/618 |
| 4,223,164 | 9/1980 | Yang et al. | 568/618 |

FOREIGN PATENT DOCUMENTS

| 26546 | 4/1981 | European Pat. Off. | |
| 930933 | 7/1963 | United Kingdom | 568/608 |

Primary Examiner—Bernard Helfin
Attorney, Agent, or Firm—Cortlan R. Schupbach, Jr.

[57] ABSTRACT

Cresylic acid ethoxylation is catalyzed by basic compounds and salts of alkaline earth metals. Ethoxylates from such reactions have narrow ethylene oxide distributions, lower pour points and lower by-products as compared to alkali base catalyzed ethoxylation. Suitable catalysts include strontium-containing and barium-containing materials. The catalyst also includes co-catalyst combinations using these materials with one or more promoters including polyols, amines, amides, carboxylic acids and phenols. The co-catalyst combinations can be preformed prior to introduction into the reaction mixture.

10 Claims, 1 Drawing Figure

ALKOXYLATION OF CRESYLIC ACIDS

This invention relates to the production of alkoxylated cresylic acids by reacting said cresylic acids in the presence of barium-containing and/or strontium-containing catalysts and promoters. More particularly, this invention relates to the production of alkoxylated cresylic acids by reacting said cresylic acids in the presence of these barium-containing and/or strontium-containing catalysts with adducting materials such as ethylene oxide and propylene oxide.

The general reaction of nonylphenol or octylphenol and adducting materials such as ethylene oxide to form alkoxylated alcohols (ethylene oxide adducts) has long been known and practiced on a commercial scale. For example, ethylene oxide adducts of nonylphenols have been used as detergents and cleaning agents, domestic and industrial laundry detergents, detergent builders, polishers, sanitizers, and dry-cleaning materials. Such material are useful as detergents and cleaning agents, detergent builders, and in formulating polishes, sanitizers and dry-cleaning materials. Alkylphenol adducts are especially good soil-suspending materials when used in detergent formulations, possessing excellent detergency, fat emulsifying power, concentration effect, chemical resistance, hard-water stability, solubility and pH value properties.

Alkoxylated cresylic acids are especially useful in the pulp and paper industry. During cellulose production the alkyl phenol adducts are especially effective in the reduction of resin content, where they accelerate the drainage of liquor from digesters and in the removal of resin from pulp. Belgium Patent 623,458 discloses the use of alkylphenol adducts as a component in an especially desirable newspaper printing ink.

Such cresylic acid adducts are useful in the textile industry, for example as a detergent component for reducing the residual fat content of wool, scouring of wool and in sizing compounds.

British Pat. No. 773,798 claims an effective fungicidal composition, especially for countering dry rot of potato tubers, containing alkylphenol adduct as dispersant. Pharmaceutical and cosmetic preparations also make use of the special properties of cresylic acid adducts as do the paint, varnish and plastics industries and those industries involved with the formulation of engine oil additives and specialty industrial lubricants.

Much literature is available in the general area of ethoxylation of alcohols. Many references are also available relating to the catalytic ability of various materials and the mechanism and kinetics of these reactions. For example, French Pat. No. 1,365,945 teaches the use of compounds containing an active hydrogen atom reacted with ethylene oxide in the presence of an alkali metal base.

Acidic catalysts in general are also known. However, in the ethoxylation of alcohols such catalysts invariably produce a distribution of various adducts. For example on surfactant applications, an adduct of too few ethylene oxide molecules is not effective because of poor solubility. In contrast, an adduct with too many ethylene oxide molecules is likewise undesirably because surface tension reduction per unit mass decreases drastically with increase in the molecular weight. Thus it has long been essential to produce and use ethoxylates with as sharp a distribution in the desired mole adduct range (3 to 10 usually) as possible. Acid-catalyzed reactions produce such alkoxylates but these catalysts produce higher levels of some harmful side products (such as dioxane) which must be separated and removed prior to use.

Russian Pat. No. 523,074 teaches that alkali metals and various carbonates can be used to catalyze adducting reactions. The side product formation in the base-catalyzed reactions is very low, but in base-catalyzed reactions the adduct distribution is undesirably broad. The result is that a large proportion of the product obtained is not useful or is less desirable because of distribution.

Representative of but not exhaustive of the art in this area is U.S. Pat. No. 3,328,467 which describes the use of zeolites and modified zeolites as catalysts in ethoxylation reactions. French Pat. No. 1,557,407 uses triethyl oxonium fluoroborate to catalyze such reactions. Indeed, the art abounds with references to alkali metal hydroxides such as sodium and potassium hydroxides, tertiary amines and sodium metal. German Offenlegungsschrift No. 2,639,564 teaches polyalkoxylation of active hydrogen compounds in the presence of a sodium fluoroborate or perchlorates of metal such as magnesium, calcium, manganese, or zinc. U.S. Pat. No. 3,969,417 uses tertiary oxonium salts as a catalyst.

U.S. Pat. No. 2,914,491 teaches the polymerization of ethylene oxide (EO) using oxides of strontium, barium and calcium. U.S. Pat. No. 3,009,887 also polymerizes EO using basic calcium phenoxide. U.S. Pat. Nos. 3,297,783 and 3,417,064 teach polymerization of various epoxides, including EO, using alcoholates of calcium, barium and strontium. U.S. Pat. No. 3,436,199 teaches ethoxylation of lignin and tannin in the presence of alkali and alkaline earth bases.

U.S. Pat. No. 3,830,850 describes adding sodium, potassium, lithium, rubidium, cesium, calcium, barium, or strontium to condense phenols with formaldehyde, then adding ethylene oxide to the condensation product in an ethoxylation reaction. However, all these materials have the disadvantages as set forth above, and do not discuss advantageous promoters for these catalysts.

Great benefit would be provided by a catalyst system which provides the low by-product levels of base catalysts yet has the narrow distribution of the preferred mole adducts obtained from acid catalysts. Such a catalyst which would promote the narrowing of the product distribution curve would contribute significantly to the intrinsic value of the ethoxylate produced. We have described such a catalyst in a copending U.S. application Ser. No. 54,089, filed July 2, 1978. However, this catalyst has an induction period ranging up to about 20 minutes at 178° C. and produces from 1 to 2% polyethylene glycol in product alcohols which while small, is still undesirably large. These catalysts have not been shown useful for cresylic acids.

It is therefore an object of the present invention to provide a catalyst system which will yield a narrow mole adduct distribution from the reaction of cresylic acids with materials such as ethylene oxide and propylene oxide while providing low levels of undesirable by-products and unreacted free alcohols, yet provide a reaction which is immediately effective with reduced induction period. Other objects will become apparent to those skilled in this art as the description proceeds.

It has now been discovered according to the present invention that alkoxylation of cresylic acids containing from about 6 to about 36 carbon atoms can be carried out by contacting the cresylic acids with an alkoxyla- tion agent in the presence of at least one material selected from the group consisting of barium metal, strontium metal, barium hydride, strontium hydride, barium oxide, strontium oxide, barium hydroxide, strontium hydroxide, hydrated barium hydroxide, hydrated strontium hydroxide, or mixtures of these. These catalysts can be used alone or together with an effective amount of a catalyst promoter or mixture of catalyst promoters. The alkoxylation reaction is normally carried out at temperatures of from about 90° C. to about 260° C. The catalyst promoter or promoters are selected from the group consisting of (a) polyols having a boiling point above 100° C. and containing a total of 2 to 30 carbon atoms; and having 2 or more hydroxyl containing compounds of the general formula wherein $R_1$, $R_2$, and $R_3$ are, independently, linear or branched acyclic groups, alicyclic groups, aryl groups, cyclic groups, or hydrogen and wherein the R-designated groups can in addition contain one or more functional groups selected from the group consisting of ether, amine, carboxyl, halogen, nitro, carbonyl, and amide;

(b) aldehydes and ketones having boiling points above 100° C. and containing a total of from 2 to 30 carbon atoms, and having one or more carbonyl containing compounds of the general formula wherein $R_1$ and $R_2$ are, independently, hydrogen, linear or branched acyclic groups, alicyclic groups, cyclic groups, or aryl groups and wherein the R-designated groups can in addition contain one or more functionalities selected from the group consisting of carboxyl, hydroxyl, ether, halogen, nitro, amine, or amide;

(c) primary, secondary or tertiary amides having a boiling point of above 100° C. and containing a total of from 1 to 30 carbon atoms and containing 1 or more amide containing compounds of the general formula wherein $R_1$, $R_2$, and $R_3$ are, independently hydrogen, linear or branched acyclic groups, alicyclic groups, cyclic groups, or aryl groups and wherein the R-designated groups can in addition contain one or more other functionalities selected from the group consisting of hydroxyl, ether, carboxyl, carbonyl, amine, nitro, or halogen;

(d) primary, secondary or tertiary amines having a boiling point above 100° C., containing from a total of 1 to 30 carbon atoms and containing 1 or more amine containing compounds of the general formula wherein $R_1$, $R_2$, and $R_3$ are, independently, hydrogen, linear or branched acyclic groups, alicyclic groups, cyclic groups, or aryl groups, and wherein the R-designated groups can in addition contain one or more functionalities selected from the group consisting of hydroxyl, ether, carbonyl, halogen, carboxyl, nitro or amide;

(e) organic acids having a boiling point of above 100° C., containing from a total of 1 to 30 carbon atoms and having 1 or more carboxylic acid containing compounds of the general formula wherein $R_1$ is hydrogen, a linear or branched acyclic group, alicyclic group, cyclic group, or aryl group and wherein the R group can in addition contain one or more functionalities selected from the group consisting of carbonyl, hydroxyl, halogen, ether, nitro, amine, or amide;

(f) phenols having a boiling point of above 100° C., containing a total of from 6 to 30 carbon atoms and having 1 or more functionalities of the general formula wherein $R_1$, $R_2$, $R_3$, $R_4$, and $R_5$ are, independently hydrogen, halogen, hydroxyl, nitro, ether, or carbonyl, linear or branched acyclic groups, alicyclic groups, cyclic groups, aryl groups, or substituted aryl groups and wherein in addition the R-designated groups can contain one or more functionalities selected from the group consisting of halogen, ether, nitro, carboxyl, carbonyl, amine, amide, or hydroxyl. Boiling points are measured at atmospheric pressure, and may be proportionally higher or lower as pressure is altered.

Representative examples of various polyol promoters effective in the process of the instant invention are:
ethylene glycol
1,2-propylene glycol
1,4-butanediol
1,6-hexanediol
1,10-decanediol
1,3-butylene glycol
diethylene glycol
diethylene glycol monobutyl ether
diethylene glycol monomethyl ether
diethyl glycol monoethyl ether
dipropylene glycol
dipropylene glycol monomethyl ether
ethylene glycol monomethyl ether
ethylene glycol monoethyl ether
ethylene glycol monobutyl ether hexylene glycol
mannitol
sorbitol
pentaerythritol
dipentaerythritol
tripentaerythritol
trimethylolpropane
trimethylolethane
neopentyl glycol
diethanolamine
triethanolamine
diisopropanolamine
triisopropanolamine
1,4-dimethylolcyclohexane
2,2-bis(hydroxymethyl)propionic acid
1,2-bis(hydroxymethyl)benzene
4,5-bis(hydroxymethyl)furfural
4,8-bis(hydroxymethyl)tricyclo[5,2,1,0] decane
tartaric acid
2-ethyl-1,3-hexanediol
2-amino-2-ethyl-1,3-propanediol
triethylene glycol
tetraethylene glycol
glycerol
ascorbic acid Representative examples of various aldehydes and ketones effective in the process of the present invention are:
lauryl aldehyde
benzaldehyde
2-undecanone
acetophenone
2,4-pentandione
acetylsalicyclic acid
ortho-chlorobenzaldehyde
para-chlorobenzaldehyde
cinnamic aldehyde
diisobutyl ketone
ethylacetoacetate
ethyl amyl ketone
camphor
para-hydroxybenzaldehyde
2-carboxybenzaldehyde
4-carboxybenzaldehyde
salicylaldehyde
octyl aldehyde
decyl aldehyde
p-methoxybenzaldehyde
p-aminobenzaldehyde
phenylacetaldehyde
acetoacetic acid
2,5-dimethoxybenzaldehyde
1-naphthyl aldehyde
terephthaldehyde Representative examples of amides which are effective promoters in the process of the instant invention are:
formamide
benzamide
acetanilide
salicylamide
acetoacetanilide
ortho-acetoacetotoluidide
acrylamide
N,N-diethyltoluamide
N,N-dimethylacetamide
N,N-dimethylformamide
phthalimide
octylamide
decylamide
laurylamide
stearylamide
N,N-dimethyllaurylamide
N,N-dimethylacrylamide
para-chlorobenzamide
para-methoxybenzamide
para-aminobenzamide
para-hydroxybenzamide
ortho-nitrobenzamide
N-acetyl-para-aminophenol
2-chloroacetamide
oxamide
N,N-methylene-bis-acrylamide Representative examples of amines which are effective promoters in the process of the present invention are:
aniline
benzylamine
hexadecylamine
triphenylamine
aminoacetic acid
anthranilic acid
cyclohexylamine
tert-octylamine
ortho-phenylenediamine
meta-phenylenediamine
para-phenylenediamine
N-acetyl-para-aminophenol
2-amino-4-chlorophenol
2-amino-2-ethyl-1,3-propanediol
ortho-aminophenol
para-aminophenol
para-aminosalicylic acid
benzyl-N,N-dimethylamine
tert-butylamine
2-chloro-4-aminotoluene
6-chloro-2-aminotoluene
meta-chloroaniline
ortho-chloroaniline
para-chloroaniline
4-chloro-2-nitroaniline
cyclohexylamine
dibutylamine
2,5-dichloroaniline
3,4-dichloroaniline
dicyclohexylamine
diethanolamine
N,N-diethylethanolamine
N,N-diethyl-meta-toluidine
N,N-diethylaniline
diethylenetriamine
diisopropanolamine
N,N-dimethylethanolamine
N,N-dimethylaniline
2,4-dinitroaniline
diphenylamine
ethyl-para-aminobenzoate
N-ethylethanolamine
N-ethyl-1-naphthylamine
N-ethyl-ortho-toluidine
N-ethylaniline
ethylenediamine
hexamethylenetetraamine
2,4-lutidine
N-methylaniline
methyl anthranilate p,p'-diaminodiphenyl methane
ortho-nitroaniline
para-nitroaniline
tert-octylamine
piperazine
ethanolamine
isopropanolamine
ortho-toluidine
para-toluidine
2,4-tolyenediamine
triethanolamine
tributylamine
triisopropanolamine
2,4-dimethylxylidine
para-methoxyaniline
nitrilotriacetic acid
N-phenyl-1-naphthylamine Representative examples of acids which are effective promoters in the process of the present invention are:
formic acid
acetic acid
valeric acid
heptanoic acid
2-ethylhexanoic acid
lauric acid
stearic acid
oleic acid
tall oil acids
hydrogenated tall oil acids
benzoic acid
salicylic acid
adipic acid
azelaic acid
fumaric acid
citric acid
acrylic acid
aminoacetic acid
para-aminosalicylic acid
anthranilic acid
butyric acid
propionic acid
ricinoleic acid
chloroacetic acid
ortho-chlorobenzoic acid
2,4-dichlorophenoxyacetic acid
tert-decanoic acid
para-aminobenzoic acid
abietic acid
itaconic acid
lactic acid
glycolic acid
malic acid
maleic acid
cinnamic acid
para-hydroxybenzoic acid
methacrylic acid
oxalic acid
myristic acid
palmitic acid
tert-pentanoic acid
phenylacetic acid
mandelic acid
sebacic acid
tallow fatty acids
hydrogenated tallow fatty acids
tartaric acid
trichloroacetic acid 2,4,5-trichlorophenoxyacetic acid
undecylenic acid
crotonic acid
pelargonic acid
acetoacetic acid
para-nitrobenzoic acid
ascorbic acid
nitrilotriacetic acid
naphthenic acids
1-naphthoic acid
trimellitic acid Representative examples of various phenols which are promoters for the catalysts of the present invention are:
phenol
ortho-cresol
meta-cresol
para-cresol
2,4-dimethylphenol
2,5-dimethylphenol
2,6-dimethylphenol
ortho-chlorophenol
meta-chlorophenol
para-chlorophenol
para-nitrophenol
para-methoxyphenol
salicylic acid
meta-hydroxyacetophenone
para-aminophenol
ortho-phenylphenol
nonylphenol
octylphenol
t-butyl-para-cresol
hydroquinone
catechol
resorcinol
pyrogallol
1-naphthol
2-naphthol
4,4'-isopropylidenediphenol (bisphenol A)
methyl salicylate
benzyl salicylate
4-chloro-2-nitrophenol
para-t-butylphenol
2,4-di-t-amylphenol
2,4-dinitrophenol
para-hydroxybenzoic acid
8-hydroxyquinoline
methyl para-hydroxybenzoate
2-nitro-para-cresol
ortho-nitrophenol
para-phenylphenol
phenyl salicylate
salicylaldehyde
p-hydroxy benzaldehyde
2-amino-4-chlorophenol
ortho-aminophenol
salicylamide
2,4-dichlorophenol
2,5-dichlorophenol
2,5-dichlorohydroquinone Certain alcohols can also act as promoters for ethoxylation of cresylic acids using the catalysts of the present invention. Such alcohols are more acidic than normal alcohols such that the association constant is greater (or the pKa is lower) than normal alcohols. Thus, these alcohol promoters would have a pKa less than 17.

These alcohols are those containing a hydroxyl group and having the formula wherein $R_1$, $R_2$ and $R_3$ are, independently, hydrogen, linear or branched acyclic groups, alicyclic groups, aryl groups, or cyclic groups and wherein the R-designated groups can in addition contain functional groups selected from the group consisting of halogen, nitro, carboxyl, amine, carbonyl, ether, and amide. The molecule can contain a total of from 2 to 30 carbon atoms.

Representative examples of these effective alcohol promoters are:
   triphenylmethanol
   trichloroethanol
   trifluoroethanol
   2-nitroethanol
   2-chloroethanol
   2,2-dichloroethanol
   2-methoxyethanol
   2-chlorocyclohexanol
   ortho-chlorobenzyl alcohol Thus, the instant invention describes a method for the alkoxylation of cresylic acids comprising contacting said cresylic acids with an alkoxylating agent in the presence of a barium-containing or strontium-containing catalyst together with an effective amount of polyol, alcohol, aldehyde, amine, amide, carboxylic acid, ketone, phenol or mixtures of these to promote the reaction. Normally, the alkoxylation agent will be ethylene oxide or propylene oxide. The instant invention can be carried out at temperatures of from about 90° C. to about 260° C. Normally, the cresylic acids reactive under the process of the instant invention will contain from about 6 to about 36 carbon atoms, but from about 6 to about 24 carbon atoms are more common.

The process of the instant invention can be carried out at ambient pressures. However, pressures of up to 100 pounds per square inch gauge (psig) can also be used. Pressures below about 60 psig are preferred. In addition, pressures below ambient can be used. It is clear that while pressure or lack of pressure is not a detriment to the process of the instant invention, it is simply more convenient to carry out the reaction in the pressure range of from about atmospheric to about 100 psig.

The instant invention is normally carried out at temperatures of from about 120° to about 260° C. However, for practical purposes, commercial operations will normally be carried out in the temperature range of from about 150° to about 200° C. Temperatures in the range of from 160° C. to about 190° C. are most preferred.

Reactions can be carried out in the presence of any alkoxylation agent which produces a mole adduct of the sort desired. Normally such agents are alpha or beta alkylene oxides. In most commercial operations, either ethylene oxide, propylene oxide, or mixtures of these will be used to produce an adduct. Of these products, ethylene oxide is most preferred.

Reaction products can have any desired content of alkoxylating agent such as ethylene oxide, but will normally range from about 20 to about 80% content of ethylene oxide (EO) based on weight. The amount of EO present in the reaction is not critical other than the minimum amount necessary to provide sufficient units to reach the mole adduct level desired for the cresylic acid being reacted.

The catalysts of the present invention are basic catalysts which provide a sharp distribution as to the mole adducts formed, while greatly reducing the amount of unreacted cresylic acid and undesirable by-products normally found in sharp distribution reactions. The instant invention optionally adds to these catalysts an effective amount of phenol, acid, amine, aldehyde, polyol, ketone, amide or alcohol in order to further reduce by-product reactions and to reduce or eliminate the induction period necessary for alkoxylation to begin.

Representation examples of strontium-containing catalysts are strontium metal, $SrH_2$, $SrO$, $Sr(OH)_2$ and $Sr(OH)_2 \cdot X\ H_2O$ where X represents the number of water molecules present. Many of these strontium compounds alone are active in the process of the instant invention and are extremely active when used with an effective amount of a co-catalyst or promoter.

Representative examples of barium-containing catalysts are barium metal, $BaH_2$, $BaO$, $Ba(OH)_2$, and $Ba(OH)_2 \cdot X\ H_2O$ where X represents the number of water molecules present. Many of these barium compounds alone are active in the process of the instant invention and are extremely active when used with an effective amount of a co-catalyst or promoter.

When used, these catalyst mixtures can be used in any desired quantity. The larger the quantity used, the more quickly the reaction goes to completion, although larger quantities do not appear to significantly alter the distribution obtained. However, for practical purposes, normally at least about 0.05 weight percent catalyst, based upon the weight of the cresylic acid to be reacted, would be present in the reaction, but normally from about 0.1 to about 5.0 weight percent is preferred and from about 0.1 to about 2.0 weight percent is most preferred. The amount of promoter or co-catalyst which should be present with the strontium and barium catalysts is generally an effective amount. The effect of the co-catalyst or promoter becomes significant at about 0.1% by weight based upon the weight of the cresylic acid to be reacted. It is logical to expect an upper limit after which the amount of promoter present will produce no additional benefits.

Normally, these promoting materials will be added to the strontium and barium catalysts in amounts ranging from about 0.1 to about 2% by weight based upon the weight of the cresylic acid. Although amounts ranging from about 0.15 to about 1.5 are preferred, and amounts ranging from about 0.3 to about 0.8% by weight based upon the weight to be reacted is most preferred. However it is very apparent that these limits can be varied substantially.

The term "cresylic acids" as used in the specification and claims refers to phenol itself and substituted phenols having a total of from 6 to about 36 carbon atoms, and mixtures of these materials. These materials are represented by the general formula wherein $R_1$, $R_2$, $R_3$, $R_4$, and $R_5$ are, independently, hydrogen, linear or branched acyclic groups, alicyclic groups, cyclic groups, aryl groups, substituted aryl groups, halogen, hydroxyl, nitro, ether or carbonyl and wherein in addition the R-designated groups can contain one or more functionalities selected from the group consisting of halogen, ether, nitro, carboxyl, carbonyl, amine, amide or hydroxyl.

The process of the present invention can be carried out by simply adding the catalyst to the combination of the cresylic acid and alkoxylating agent under sufficient conditions for alkoxylation to occur. This is true whether the catalysts are used alone or in combination with a material which promotes their activity. However, in order to further increase catalytic activity, these catalysts may be preformed by simply heating the catalytic metal compound and promoter together for a time and at a temperature sufficient to obtain the preformed material. Normally such reaction time ranges up to about 2 hours but from about ½ to about 1 hour is preferred. The reaction temperatures range up to about 175° C. but reaction temperatures from about 100° C. to about 150° C. are preferred.

For handling ease a solvent effective for either or both the catalytic metal compound and promoter can be used. Such solvents are entirely optional and not critical in any manner to the preforming of the catalyst of the instant invention. Such solvents can be removed by heating until the preformed catalyst is obtained as a solid if desired, or can be used as a carrier for the preformed catalyst for handling ease. Heating the preformed catalyst for a time and at a temperature sufficient to remove bound water is likewise preferred but is not critical.

In many cases, the solvent is a material capable of promoting the alkoxylation reaction and of producing a preformed catalyst. This is true when examining the materials which can be used to promote the process of the instant invention. For example, the highly active phenolic material as promoter can act to form a preformed catalyst and likewise promote the reaction with phenols itself. For example, a phenol catalyst can be preformed with a barium or strontium material and effectively promote the alkoxylation of phenol itself.

Representative but non-exhaustive examples of phenolic compounds which, alone or in mixture, form the cresylic acids effectively alkoxylated in the process of the present invention are:

phenol
ortho-cresol
meta-cresol
para-cresol
2,4-dimethylphenol
2,5-dimethylphenol
2,6-dimethylphenol
2,3-dimethylphenol
ortho-chlorophenol
meta-chlorophenol
para-chlorophenol
para-nitrophenol
para-methoxyphenol
salicylic acid
meta-hydroxyacetophenone
para-aminophenol
ortho-phenylphenol
nonylphenol
octylphenol
t-butyl-para-cresol
hydroquinone
catechol
resorcinol
pyrogallol
1-naphthol
2-naphthol
4,4'-isopropylidenediphenol (bisphenol A)
methyl salicylate
benzyl salicylate
4-chloro-2-nitrophenol
para-t-butylphenol
2,4-di-t-amylphenol
2,4-dinitrophenol
para-hydroxybenzoic acid
8-hydroxyquinoline
methyl para-hydroxybenzoate
2-nitro-para-cresol
ortho-nitrophenol
para-phenylphenol
phenyl salicylate
salicylaldehyde
p-hydroxy benzaldehyde
2-amino-4-chlorophenol
ortho-aminophenol
dodecylphenol
octyl cresol
dioctyl cresol
dinonylphenol
salicylamide
2,4-dichlorophenol
2,5-dichlorophenol
2,5-dichlorohydroquinone Thus, the instant invention provides for the production of highly efficient cresylic acid alkoxylates from phenolic materials either used alone or in mixtures in a novel, highly unexpected manner. These cresylic acids contain from about 6 to about 36 carbon atoms although from about 6 to about 20 carbon atoms will be more common.

The invention is more concretely described with reference to the examples below wherein all parts and percentages are by weight unless otherwise specified. The examples are provided to illustrate the instant invention and not to limit it.

EXAMPLE 1

Figure 1:
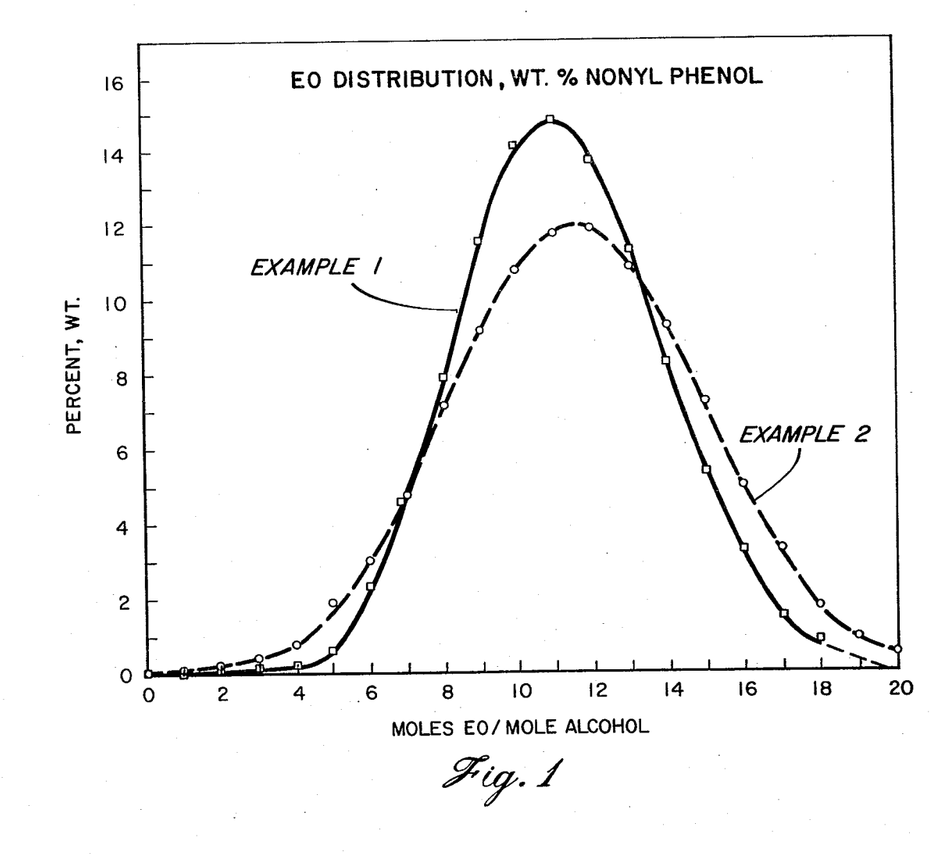

A 600 cubic centimeter (cc) stainless steel reactor was charged with 90 grams of nonylphenol and 0.3 gram of Ba(OH)$_2$.H$_2$O. After purging with nitrogen at 250 cc per minute for 1 hour at a temperature of 150° C., the reactor was evacuated and temperature raised to about 170° C. Ethylene oxide (EO) was then introduced to a total pressure of about 40 pounds per square inch gauge (psig) EO uptake of 210 grams was allowed to proceed at this pressure. After ethoxylation, the catalyst was neutralized. Ethoxylation required 102 minutes for completion. The product contained less than 0.1% unreacted nonylphenol and had a pour point of 55° F. A preferred, more peaked EO distribution was obtained as compared to an alkali-catalyzed reaction is shown in FIG. 1.

EXAMPLE 2

A comparative experiment was carried out as described in Example 1 except that 120 grams of nonylphenol was used and 0.15 gram of NaOH was used. An EO addition of 280 grams was completed in 142 minutes. The product contained less than 0.1% unreacted nonylphenol and had a pour point of 65° F. The ethylene oxide distribution is shown in FIG. 1. A comparison of Example 1 and Example 2 shows that the catalysts of the instant invention provide a much more peaked distribution than the alkali metal catalysts previously known for alkoxylations.

EXAMPLE 3

An experiment was carried out as described in Example 1 except that 0.8 gram of Sr(OH)$_2$.8H$_2$O was used as the catalyst. Ethylene oxide addition to a level of 210 grams was complete in 143 minutes. A narrow ethylene oxide adduct distribution was produced and the product contained a low level of unreacted nonylphenol.

EXAMPLE 4

An experiment was carried out as described in Example 1 except that 120 grams of phenol and 0.8 gram of Sr(OH)$_2$.8H$_2$O was used as a catalyst. A weight of 180 grams EO was added in 54 minutes. The product had a narrow EO adduct distribution and a very low level of unreacted phenol.

EXAMPLE 5

An experiment was carried out as described in Example 1 except that propylene oxide (PO) is used as the alkoxylating agent. The use of PO requires more time to complete than a comparable preparation to a similar adduct level using EO. After propoxylation the catalyst is neutralized. The resulting product has a narrow peaked adduct distribution and a low level of unreacted nonylphenol when compared to similar preparations using alkali metal catalysts.

EXAMPLE 6

An experiment was carried out as described in Example 1 except that 150 grams of 2,3-dimethylphenol was used and 0.8 gram of Sr(OH)$_2$.8H$_2$O was used as catalyst. A weight of 150 grams EO was added in 98 minutes. The product had a narrow EO adduct distribution and a very low level of unreacted 2,3-dimethylphenol.

EXAMPLE 7

An experiment was carried out as described in Example 1 except that 120 grams para-chlorophenol and 0.8 gram Sr(OH)$_2$.8H$_2$O was used. The addition of 180 grams EO was completed in 107 minutes. A narrow peaked EO adduct distribution was obtained and the level of unreacted para-chlorophenol was very low.

EXAMPLE 8

An experiment was carried out as described in Example 1 except that 120 grams of phenol and 0.60 gram of preformed catalyst prepared from 5.0 grams Ba(OH)$_2$.8H$_2$O and 6.9 grams of heptanoic acid was used. A weight of 10.1 grams of solid preformed catalyst was obtained. Propylene oxide at a level of 180 grams is added. The propylene oxide requires more time to complete to a comparable adduct level than a similar preparation using EO. The propylene oxide adduct distribution is narrow and peaked. The level of unreacted nonylphenol is very low.

Although exemplified as batch reactions, the catalyst and promoters of the present invention are extremely well suited to continuous reaction methods. The reaction products are of extremely high quality and quantity.

It is apparent that the instant invention provides a method for obtaining high mole adduct alkoxylates of cresylic acids which have a very narrow highly desirable distribution range. In addition, the products have low amounts of by-products and unreacted cresylic acids. The reaction rate is desirably fast. The optional promoters of the present invention, whether added freely or as a preformed catalyst, help speed reaction rates while maintaining high quality levels.

While certain embodiments and details have been shown for the purpose of illustrating this invention, it will be apparent to those skilled in this art that various changes and modifications may be made herein without departing from the spirit or scope of the invention.

We claim:
1. A method for the alkoxylation of cresylic acids containing from about 6 to about 36 carbon atoms comprising contacting said cresylic acids with an alkoxylating agent at temperatures from about 120° C. to about 260° C. in the presence of basic barium-containing and strontium-containing materials selected from the group consisting of strontium metal, barium metal, strontium hydride, barium hydride, strontium oxide, barium oxide, strontium hydroxide, barium hydroxide, strontium hydroxide.XH$_2$O and barium hydroxide.XH$_2$O wherein X represents the number of water molecules present, and wherein the cresylic acids are a phenolic compound or a mixture of phenolic compounds having the general formula wherein R$_1$, R$_2$, R$_3$, R$_4$, and R$_5$ are, independently, hydrogen, linear or branched acyclic groups, alicyclic groups, cyclic groups, aryl groups, substituted aryl groups, halogen, hydroxyl, nitro, or carbonyl and wherein in addition the R-designated groups can contain one or more functionalities selected from the group consisting of halogen, nitro, carboxyl, carbonyl, amine, amide, or hydroxyl and wherein in addition from about 0.1 to about 2.0 weight percent by weight based on the weight of cresylic acid of a catalyst promoter or mixture of catalyst promoters is used, wherein the catalyst promoter is selected from the group consisting of
(a) aldehyde and ketone promoters containing one or more carbonyl containing compounds of the general formula wherein R$_1$, and R$_2$ are, independently, linear or branched acyclic groups, alicyclic groups, cyclic groups, aryl groups, or hydrogen, and wherein the R-designated groups in addition can contain one or more functional groups selected from the group consisting of hydroxyl, carboxyl, carbonyl, amine, nitro or halogen;
(b) amide promoters containing one or more amide containing compounds of the general formula wherein R₁, R₂, and R₃ are, independently, hydrogen, linear or branched acyclic groups, alicyclic groups, cyclic groups or aryl groups and wherein the R-designated groups can in addition contain one or more functional groups selected from the group consisting of hydroxyl, carboxyl, carbonyl, amine, nitro or halogen;

(c) amine promoters containing one or more amine containing compounds of the general formula wherein R₁, R₂, and R₃ are, independently, hydrogen, linear or branched acyclic groups, alicyclic groups, cyclic groups, or aryl groups, and wherein the R-designated groups can in addition contain one or more functional groups selected from the group consisting of hydroxyl, carbonyl, halogen, carboxyl, nitro, or amide;

(d) organic acid promoters containing one or more carboxylic acid containing compounds of the general formula wherein R₁ is a hydrogen, linear or branched acyclic group, alicyclic group, cyclic group, or aryl group and wherein R can in addition contain one or more functional groups selected from the group consisting of carbonyl, hydroxyl, halogen, nitro, amine, or amide.

2. A method as described in claim 1 wherein the alkoxylation is carried out using ethylene oxide, propylene oxide, or mixtures of these.

3. A method as described in claim 2 wherein the reaction is carried out at a pressure of up to about 100 pounds per square inch gauge.

4. A method as described in claim 3 wherein ethylene oxide, propylene oxide or mixtures thereof are used as the alkoxylation agent and a mole adduct ratio ranges from about 20 weight percent to about 80 weight percent of the alkoxylated product.

5. A method as described in claim 4 wherein the barium or strontium-containing catalyst or mixture thereof is present in an amount of from about 0.05 to about 5.0% by weight based upon the cresylic acid to be reacted.

6. A method as described in claim 1 when carried out in a continuous reaction.

7. A method as described in claim 1 wherein the aldehydes and ketones are selected from the group consisting of
lauryl aldehyde
benzaldehyde
2-undecanone
acetophenone
2,4-pentandione
acetylsalicyclic acid
ortho-chlorobenzaldehyde
para-chlorobenzaldehyde
cinnamic aldehyde
diisobutyl ketone
ethylacetoacetate
ethyl amyl ketone
camphor
para-hydroxybenzaldehyde
2-carboxybenzaldehyde
4-carboxybenzaldehyde
salicyaldehyde
octyl aldehyde
decyl aldehyde
p-methoxybenzaldehyde
p-aminobenzaldehyde
phenylacetaldehyde
acetoacetic acid
2,5-dimethoxybenzaldehyde
1-naphthyl aldehyde
terephthaldehyde.

8. A method as described in claim 1 wherein the amides are selected from the group consisting of
formamide
benzamide
acetanilide
salicylamide
acetoacetanilide
ortho-acetoacetotoluidide
acrylamide
N,N-diethyltoluamide
N,N-dimethylacetamide
N,N-dimethylformamide
phthalimide
octylamide
decylamide
laurylamide
stearylamide
N,N-dimethylollaurylamide
N,N-dimethylacrylamide
para-chlorobenzamide
para-aminobenzamide
para-hydroxybenzamide
ortho-nitrobenzamide
N-acetyl-para-aminophenol
2-chloroacetamide
oxamide
N,N-methylene-bis-acrylamide.

9. A method as described in claim 1 wherein the amines are selected from the group consisting of
aniline
benzylamine
hexadecylamine
triphenylamine
aminoacetic acid
anthranilic acid
cyclohexylamine
tert-octylamine
ortho-phenylenediamine
meta-phenylenediamine
para-phenylenediamine
N-acetyl-para-aminophenol
2-amino-4-chlorophenol
2-amino-2-ethyl-1,3-propanediol
ortho-aminophenol
para-aminophenol
para-aminosalicyclic acid benzyl-N,N-dimethylamine
tert-butylamine
2-chloro-4-aminotoluene
6-chloro-2-aminotoluene
meta chloroaniline
ortho-chloroaniline
para-chloroaniline
4-chloro-2-nitroaniline
cyclohexylamine
dibutylamine
2,5-dichloroaniline
3,4-dichloroaniline
dicyclohexylamine
diethanolamine
N,N-diethylethanolamine
N,N-diethyl-meta-toluidine
N,N-diethylaniline
diethylenetriamine
diisopropanolamine
N,N-dimethylethanolamine
N,N-dimethylaniline
2,4-dinitroaniline
diphenylamine
ethyl-para-aminobenzoate
N-ethylethanolamine
N-ethyl-1-naphthylamine
N-ethyl-ortho-toluidine
N-ethylaniline
ethylenediamine
hexamethylenetetraamine
2,4-lutidine
N-methylaniline
methyl anthranilate
p,p'-diaminodiphenyl methane
ortho-nitroaniline
para-nitroaniline
tert-octylamine
piperazine
ethanolamine
isopropanolamine
ortho-toluidine
para-toluidine
2,4-tolyenediamine
triethanolamine
tributylamine
triisopropanolamine
2,4-dimethylxylidine
para-methoxyaniline
nitrilotriacetic acid
N-phenyl-1-naphthylamine.

10. A method as described in claim 1 wherein organic acids are selected from the group consisting of:
formic acid
acetic acid
valeric acid
heptanoic acid
2-ethylhexanoic acid
lauric acid
stearic acid
oleic acid
tall oil acids
hydrogenated tall oil acids
benzoic acid
salicyclic acid
adipic acid
azelaic acid
fumaric acid
citric acid
acrylic acid
aminoacetic acid
para-aminosalicylic acid
anthranilic acid
butyric acid
propionic acid
ricinoleic acid
chloroacetic acid
ortho-chlorobenzoic acid
2,4-dichlorophenoxyacetic acid
tert-decanoic acid
para-aminobenzoic acid
abietic acid
itaconic acid
lactic acid
glycolic acid
malic acid
maleic acid
cinnamic acid
para-hydroxybenzoic acid
methacrylic acid
oxalic acid
myristic acid
palmitic acid
tert-pentanoic acid
phenylacetic acid
mandelic acid
sebacic acid
tallow fatty acids
hydrogenated tallow fatty acids
tartaric acid
trichloroacetic acid
2,4,5-trichlorophenoxyacetic acid
undecylenic acid
crotonic acid
pelargonic acid
acetoacetic acid
para-nitrobenzoic acid
ascorbic acid
nitrilotriacetic acid
naphthenic acids
1-naphthoic acid
trimellitic acid.

* * * * *